(12) United States Patent
Viera

(10) Patent No.: US 7,962,017 B2
(45) Date of Patent: Jun. 14, 2011

(54) DEVICE FOR THE EVAPORATION OF VOLATILE SUBSTANCES, IN PARTICULAR OF AROMATICS AND/OR INSECTICIDES

(75) Inventor: Pedro Queiroz Viera, Cascais (PT)

(73) Assignee: C.T.R. Consultoria Tecnica E Representacoes, Parede (PT)

( * ) Notice: Subject to any disclaimer, the term of this patent is extended or adjusted under 35 U.S.C. 154(b) by 637 days.

(21) Appl. No.: 10/594,415

(22) PCT Filed: Mar. 26, 2004

(86) PCT No.: PCT/EP2004/003193
§ 371 (c)(1),
(2), (4) Date: Jul. 16, 2007

(87) PCT Pub. No.: WO2005/092400
PCT Pub. Date: Oct. 6, 2005

(65) Prior Publication Data
US 2007/0280653 A1 Dec. 6, 2007

(51) Int. Cl.
*F24F 3/14* (2006.01)
*F24F 6/08* (2006.01)
(52) U.S. Cl. .................................... 392/392; 392/395

(58) Field of Classification Search .......... 392/386–406;
239/34–60; 219/385, 391–401
See application file for complete search history.

(56) References Cited

U.S. PATENT DOCUMENTS

| | | | |
|---|---|---|---|
| 3,410,488 A * | 11/1968 | Sadakichi | 239/55 |
| 4,375,586 A * | 3/1983 | Ueda | 219/714 |
| 4,870,254 A * | 9/1989 | Arabori et al. | 219/400 |
| 6,859,615 B2 * | 2/2005 | Yip et al. | 392/395 |

* cited by examiner

*Primary Examiner* — Sang Y Paik
(74) *Attorney, Agent, or Firm* — Cort Flint

(57) ABSTRACT

An evaporation device for evaporating volatile substances such as aromatics and/or insecticides comprising a housing; and a receptacle arrangement carried by the housing having two receiving chambers for substances to be evaporated. Wicks inserted into the receiving chambers include wick ends protruding from the receiving chambers. A heater arrangement is carried in the housing for providing heat to the protruding wick ends for producing an evaporated substance. At least one blower is provided for generating a targeted air stream to entrain the evaporated substance. A control unit is provided for controlling the heater arrangement to evaporate the substances and for controlling the blower to be switched on at defined evaporation times.

29 Claims, 6 Drawing Sheets

DEVICE FOR THE EVAPORATION OF VOLATILE SUBSTANCES, IN PARTICULAR OF AROMATICS AND/OR INSECTICIDES

BACKGROUND OF THE INVENTION

This invention relates to a device for the evaporation of volatile substances, in particular of aromatics and/or insecticides.

Devices for the evaporation of volatile substances are generally known wherein a receptacle containing a volatile substance is inserted into a housing. This receptacle has a wick which conveys the substance to be evaporated from the receptacle by means of the capillary effect and which is there given off into the surroundings. To increase the rate of volatilization by evaporation, it is further known to arrange the end of the wick protruding from the receptacle, adjacent to a heating element, e.g., a ceramic heater. The substance conveyed upward via the wick will be volatized even faster by means of evaporation due to the heat radiated by the heating element and can escape through ventilation slots in the housing into the environment. A constant amount of the corresponding substance is released into the environment.

One problem which can occur with the evaporation of aromatics with persons in a room, a so-called habituation effect can occur relatively fast, i.e., the persons no longer notice the aromatic. To prevent this habituation effect, it is desirable to periodically volatize for a short period a different aromatic, either additionally or alone, to generate a different perception of scent which will prevent habituation. This should be fast and effectively possible, especially with larger rooms as well, which is not the case, for example, with the known devices from WO 01/05442 Al.

An additional problem which can occur in particular with the evaporation of insecticides for some types of insects, e.g., flies, a relatively high concentration of the corresponding insecticide might be required to achieve the desired effect. With the above-mentioned conventional evaporation devices, relatively high concentrations can only be achieved through continuous insecticide evaporation over a relatively long period of time. Such prolonged evaporation is undesirable for various reasons.

It is an object of this invention to create a device for the evaporation of volatile substances with several receiving chambers separated from each other for volatile substances which enables, especially for a fast prevention of habituation effects or, respectively, for a fast concentration increase when changing over to specific aromatics and/or insecticides, a particularly fast and effective evaporation of the volatile substances for the most varied purposes of application.

SUMMARY OF THE INVENTION

The above objectives are achieved by providing a device with a blower switched on either manually or via timer equipment, wherein the flow of evaporated substance escaping from the housing will be increased compared with the flow when the blower is not switched on. This will result in a faster and better distribution of aromatics and/or insecticides into the environment. By means of the control unit, the blower can be controlled so that, especially at the beginning of the evaporation of a desired substance or, respectively, after switching on or over to the evaporation of different substances by means of the blower, an air stream will be generated which will enable a faster and more effective distribution of evaporated substances into the environment. Thus, with the evaporation of aromatics or, respectively, perfumes, it can be very fast and effectively realized when switching on or over to another aromatic that a desirable different scent perception will be generated in the room for a prevention of the habituation effect. It can also be provided, for example, that in one of the receiving chambers, an insecticide will be received, and in another receiving chamber, an aromatic will be received. This provides, in combination with a manual and/or timer-controlled activation, for example, that during the day only the aromatic will be evaporated whereas at night only the insecticide will be evaporated. By switching on the blower manually or timer-controlled, a fast change-over to the other condition can be achieved in the simplest manner. Alternatively, at specifically defined times, the simultaneous evaporation of aromatic and insecticide can also occur. Especially when the insecticide as such would have a scent which is considered unpleasant. Also, when switching over from the evaporation of one insecticide to the evaporation of another insecticide required at a high concentration, the required high concentration can be made available very fast due to the specific switching on the blower. That is comparable in efficiency with the burst of spray from a spray can.

The control unit can be designed as regulating equipment by which, in combination with a corresponding sensor system. a desired concentration of the aromatic and/or the insecticide can be regulated.

The device according to the invention thus creates a very fast and effective evaporation of the individual substances as a function of specific time intervals and in combination with an evaporation device having multiple receiving chambers for volatile substances to be evaporated. A blower can be individually or specifically switched on for the various cases of application to enhance the evaporation process.

Advantageously, the blower has at least one by means of which a targeted air stream can be generated in a simple manner. The air stream acting as a carrier gas entrains the evaporated substance away from a near wick end evaporation area, and will convey it to at least one air outlet area or to ventilation slots provided on the housing. Such a structure is especially easy and economical to make.

A structure is especially advantageous in which several blowers are assigned to each evaporation area or wick end. In switched-on condition, the blower will apply a targeted air stream to the accordingly assigned evaporation area or wick end. Thus, a particularly targeted evaporation of the desired substance or substances will be possible. The blower can be switched on so that at the beginning, and/or in the middle of an evaporation process, a targeted air stream can be applied to one selected wick end area or to several selected wick end areas.

In accordance with another embodiment the air stream may be directed so that it does not impinge upon the heater element so as not to cool it off. Accordingly, the air stream advantageously impinges upon the evaporated substance near the wick end evaporation area at a distance from the heater element and/or upon the wick end protruding from the heater element.

In accordance with another embodiment, it can be provided, especially for avoiding a blower stream to the heater arrangement, that the blowers are capsulated to incorporate them in a separate/housing. Especially with several blowers, it may be advantageous that every is separately capsulated to enable a targeted air stream in the direction of the assigned evaporation area or wick end. To achieve high air stream velocities a air stream passage opening of at least one housing may be designed as a tapered nozzle.

The heater arrangement may be arranged in the housing of the evaporator device, preferably in a encapsulation or housing, that it does not apply heat to the wick end but instead that the air stream will be heated so that a hot air stream will then impinge upon the wick end which is soaked with the substance to be evaporated. This can also be used in evaporation devices in which merely one single receptacle with a single receiving chamber will be used for a single substance to be evaporated. Such a heater arrangement can be provided for wick heating, in addition to a heater arrangement. Even a combined double function heater arrangement is conceivable for heating not only the wick but also the air stream.

In accordance with a preferred embodiment, different heater arrangements formed by a single heating block on which several separate heating block areas are formed. Alternatively, however, the heater arrangement can also be formed by individual heaters being placed at a distance from each other. The individual heaters or the heating block areas are either thermally insulated by their distance to each other or by corresponding measures, such as, e.g., air gaps. In this way, they will mutually affect each other as little as possible and can also be heated separately from the other heaters or, respectively, the heating block areas by controlling the corresponding heater or, respectively, the corresponding heating block area by means of the control unit. Each of these heating block areas or heaters, respectively, have a wick recess into which the corresponding wick end of an assigned wick will protrude. Adjacent to the wick recesses on the heater or, respectively, in the heating block areas, electrical heating elements are provided which are controllable by means of the control unit. These electrical heating elements are preferably electrical resistance elements, e.g., PTC resistance elements or also sheet resistances which are cut in or ground in accordingly coordinated to a substance to be evaporated, such as known from EP 1 195 169 Al, for example.

The control unit can have a programmable microprocessor, especially with a timer device, which is programmable such that the desired evaporation situations can be simply programmed so that at specific pre-defined times, prescribed evaporation processes will take place for a defined period of time. Such a microprocessor is advantageously integrated into the housing, with programming also possibly being done from outside of the housing, if applicable. The control unit may also have a manual switch arrangement on the housing which is accessible from the outside by means of which the heater arrangement and the blower can be manually switched on. For this, one combined manual switch can be provided or separate manual switches as well, depending on a desired evaporation application. In particular, the combination of one or, manual switch will be possible with a timer device of the control unit so that upon activation of a manual heater switch for a specific heating block or heater via the timer device, a blower will be switched on for a specific, definable time(s).

In accordance with another preferred embodiment the wick end/heater area in the housing can be capsulated, to ensure that an air stream generated by the blower will not directly impinge upon the heater arrangement but merely upon a wick end area. In the case of such wick arrangements where the wick end is generally flush with the surface in the heater or heating block, air slots can be provided in the encapsulation or screening of the corresponding housing parts which effect the encapsulation. The volatilizing substance can escape through the air slots starting from the wick end area into the area in which it impinges upon the air stream.

A mixing chamber can also be formed on the housing, and the receptacle arrangement can be formed by several separate receptacles which form the individual receiving chambers or by a single receptacle which is formed of several chambers.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Referring now in more detail to the drawings, the invention will now be described in more detail.

Figure 1:
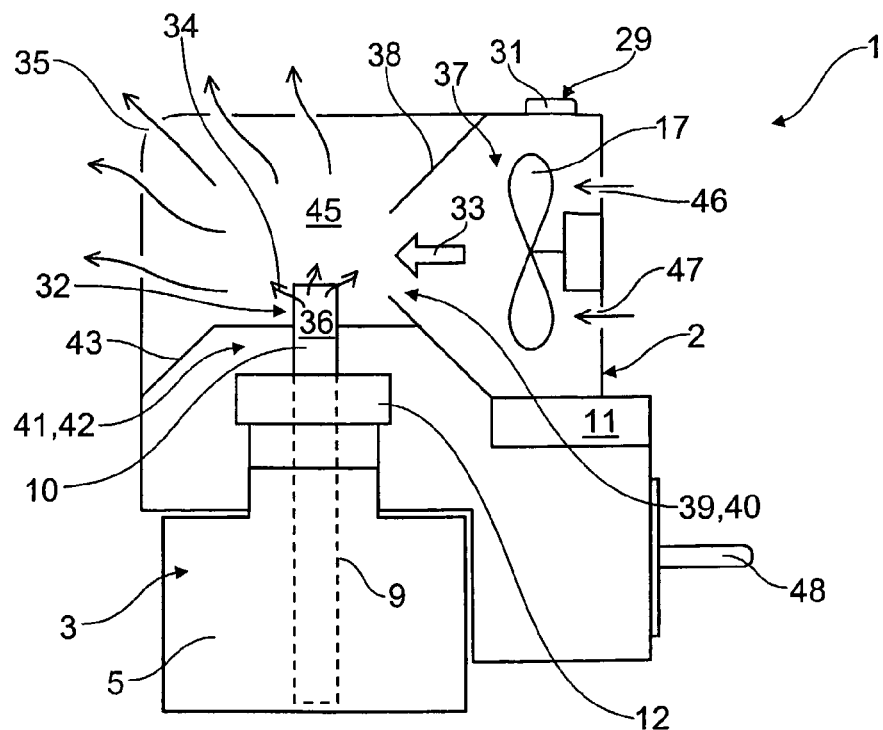
FIG. 1 is a schematic diagram illustrating a first embodiment of an evaporation device according to the invention, in a side view.

FIG. 1 shows schematically a first embodiment of an evaporation device 1 having a multi-part housing 2 in which a receptacle arrangement 3 can be inserted and retained in a generally known manner. As can be taken from the schematic front view of FIG. 2, this receptacle arrangement 3 consists of a first receptacle 4 and a second receptacle 5 for containing different substances to be evaporated, e.g., two aromatics or two insecticides, but also one aromatic and one insecticide. Alternatively to such a receptacle arrangement 3 with two separate receptacles 4, 5 forming the receiving chambers for the substances to be evaporated, a receptacle arrangement 6 in accordance with FIG. 10 may be provided as well, where one single receptacle has a first receiving chamber 7 and a second receiving chamber 8 for the substances to be evaporated.

Figure 2:
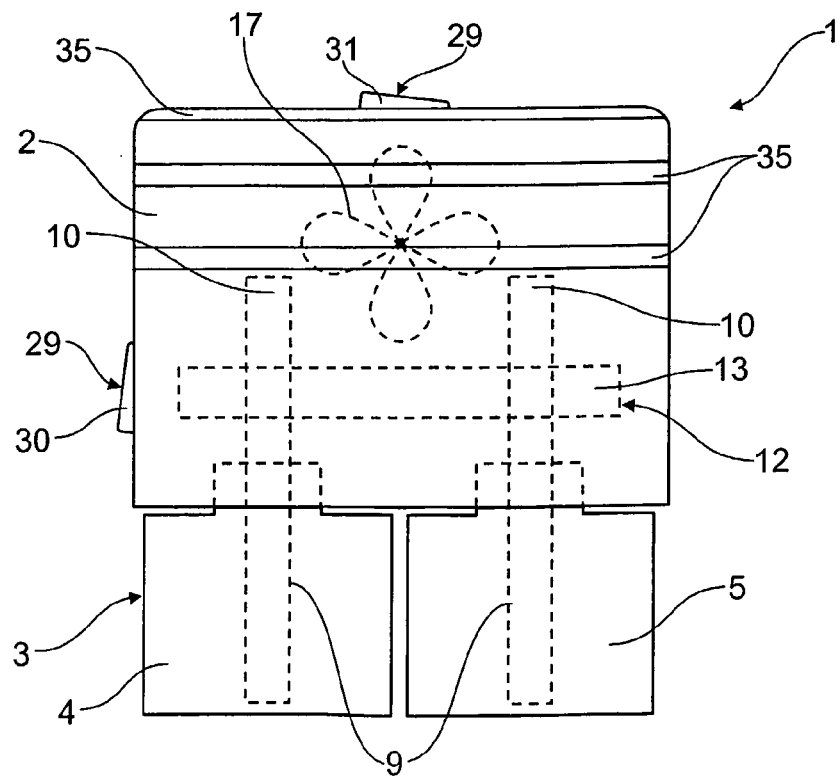
FIG. 2 is a schematic front view of the evaporation device according to FIG. 1.
Figure 10:
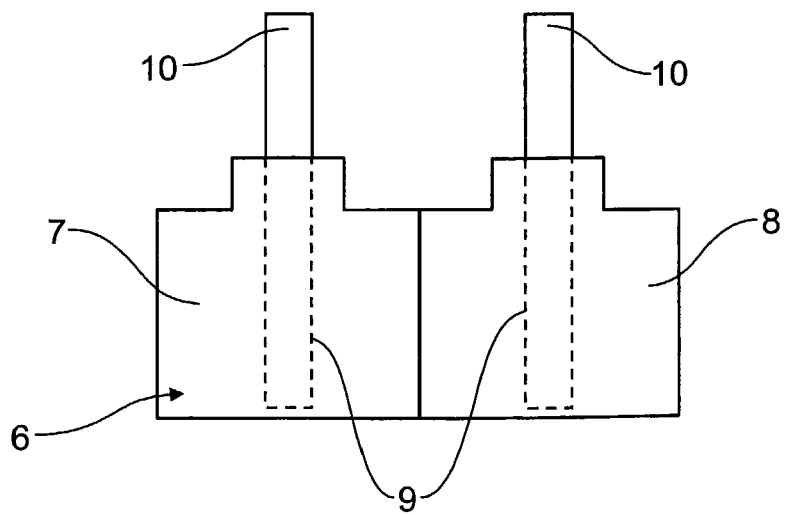
FIG. 10 an alternative embodiment of a receptacle arrangement formed by a single receptacle with two receiving chambers.

As can be further taken from FIGS. 1 and 2 or 10, a wick 9 is inserted into each receptacle 4, 5 or, respectively, into each receiving chambers 7, 8. The wick protrudes with a wick end 10 from corresponding receptacle 4,5 or, respectively, corresponding receiving chamber 7, 8.

Figure 8:
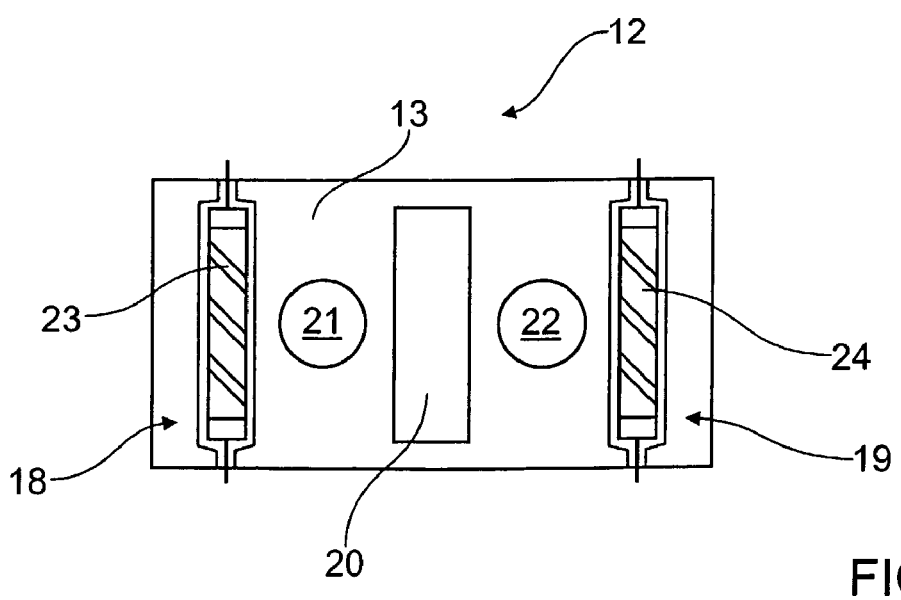
FIG. 8 is a schematic basic presentation of a plan view of a heater arrangement formed by one heating block, in accordance with the embodiments of FIGS. 1 to 6.

As Is shown only In a schematic and basic manner in FIGS. 1 and 2, a heater arrangement 12 is assigned to the wick ends. As can be seen in FIG. 8, the heating arrangement is formed by a single heating block 13 having two heating block areas 18 and 19 thermally isolated front each other by means of an air slot 20. In the first heating block area 18, a first wick recess 21 is formed which is associated with a first electrical resistance element 23 at first heating block area 18.

Correspondingly, on the opposite side of the air slot 20 at a second heating block area 19, a second wick recess 22 is associated with a second electrical resistance element 24.

Heating block 13 is advantageously formed of a ceramic material with two resistance elements 23, 24 (preferably so-called film resistors) disposed and cemented in the corresponding recesses of heating block 13.

Wick recesses 21, 22 are formed as passage holes in heating block 13 through which corresponding wick ends 10 pass to more or less protrude from heating block 13, as shown schematically.

As can be further taken from FIG. 1, wick end 10 protrudes with a wick end area 36 from heating block 13. A blower 17 is carried within the housing to produce an air stream 33 for forcing the evaporated substance out of the housing into the associated interior space. To prevent air stream 33 from blowing against and cooling heating block 13, a heating area 41 of wick end 10 is preferably enclosed by means of a housing wall 43. That is, a partial housing area 42 is formed from which only wick end area 36 of wick end 10 will protrude. Thus, heating block 13 is screened from air stream 33 of blower 17 so air stream 33 can only impinge upon the wick end area 36. Blower 17 may be a fan, cage blower, ventilator, or any other suitable device or arrangement for supplying an air stream.

Blower 17 is screened off or enclosed by means of at least one housing wall 38 forming a tapered nozzle 40 in the area of air stream passage 39. Nozzle area 40 provides a targeted air stream 33 with a high air velocity when blower 17 is switched on. When activated, the blower takes in ambient air via the air entry openings 46 and 47. Heater arrangement 14 and blower 17 are coupled with a control unit 11, shown schematically, having a manual switching arrangement 29 with a manual heater switch 30, shown in FIG. 2, and a manual blower switch 31 shown in FIGS. 1 and 2.

Heating block areas 18, 19 can be controlled by means of the manual heater switch 30, depending on the switching position. The areas are advantageously controllable so that, starting from an off-position in which none of heating block areas 18, 19 are heated, one of heating block areas 18, 19 or both heating block areas 18, 19, can be simultaneously heated.

To achieve, especially at the beginning of an evaporation, a particularly fast and effective distribution of the respectively desired substance or substances to be evaporated, Blower 17 can also be switched on via the manual switch 31 or alternatively timer-controlled upon actuation of the manual heater switch 30, so that air stream 33 will be generated. In the wick end evaporation area 32, the air stream impinges upon the evaporated substance 34 and entrains it in as a carrier stream to air outlet areas 35 or the ventilation slots on housing 2 where the substance escapes into the environment.

Figure 3:
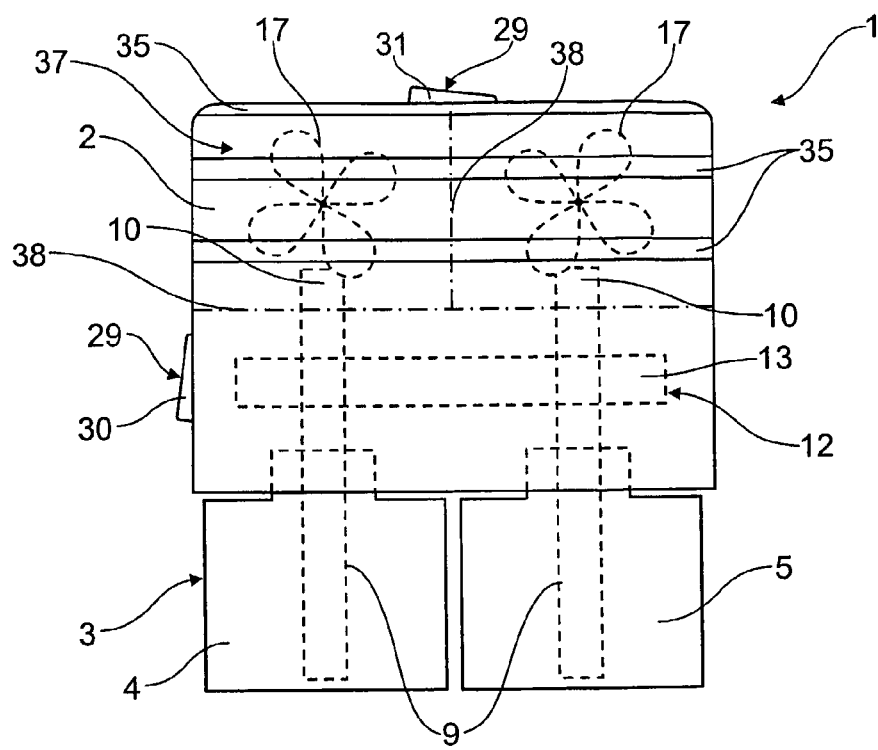
FIG. 3 is a schematic front view according to FIG. 2 with an alternative embodiment of the evaporation device, having two s.

In FIG. 2, a first embodiment of evaporation device 1 is presented in a front view of the structure according to FIG. 1 wherein one blower 17 is provided for generating a targeted air stream 33. However, in accordance with another embodiment, presented in FIG. 3, an arrangement with two blowers 17 can also be provided. One of the blowers is assigned to each wick end 10. In such a case, as also shown in FIG. 3, two blowers 17 can also form two separate partial housing areas 37 by means of a corresponding design of the housing walls 38 in this area. With this embodiment, individual blowers 17 can be switched on in a targeted manner so that with an evaporation of the substance incorporated in the first receptacle 4, only blower 17, on the left of FIG. 3, will be switched on via the manual switch 31. Preferably this provides a desired, so-called boost or blast time in which a particularly fast and effective distribution of the substance to be evaporated into the environment will be desired. To prevent, for example, a habituation effect, the other substance incorporated in second receptacle 5 can then be additionally, or even alone, evaporated for a specified period of time. This can be accomplished by means of the manual switches 30, 31 or by timer control as a function of a manual switch actuation. Blower 17, on the right as shown in FIG. 6, is correspondingly switched on at least intermittently.

Figure 4:
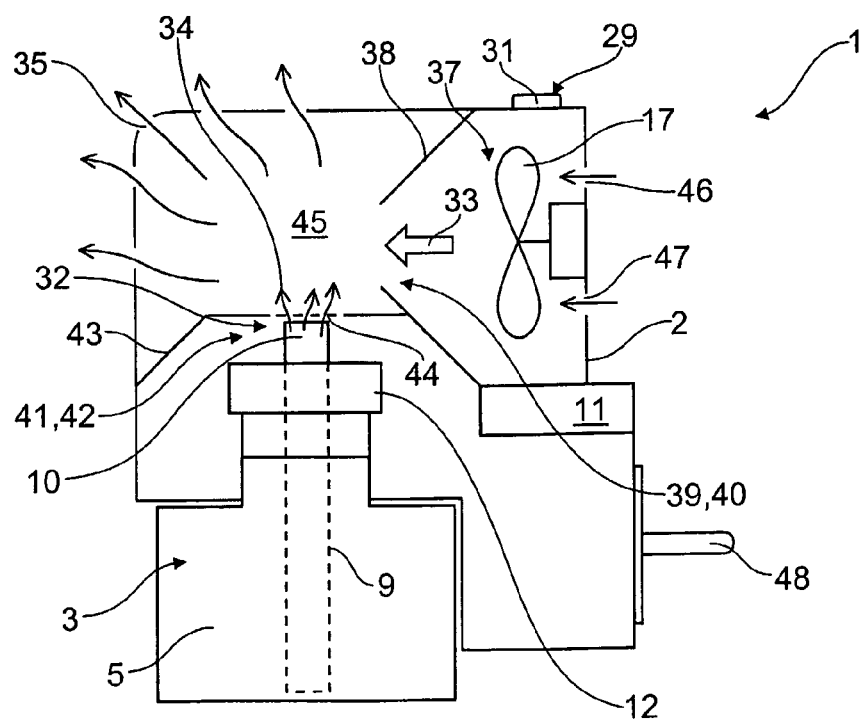
FIG. 4 is a schematic diagram illustrating an embodiment of the evaporation device, alternative to FIG. 1, in a side view.
Figure 5:
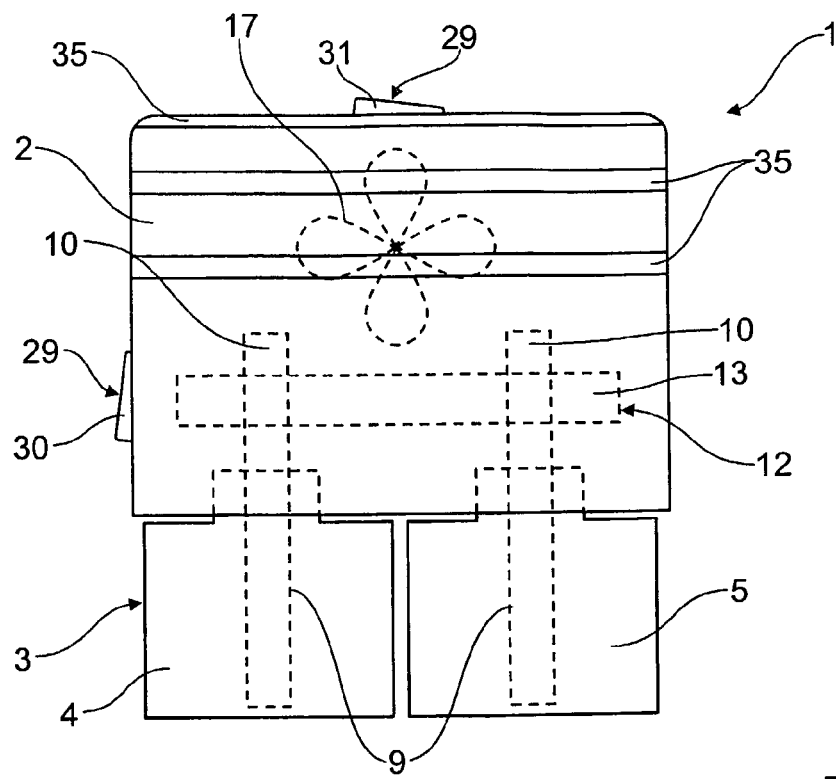
FIG. 5 is a schematic front view of the evaporation device according to FIG. 4.
Figure 6:
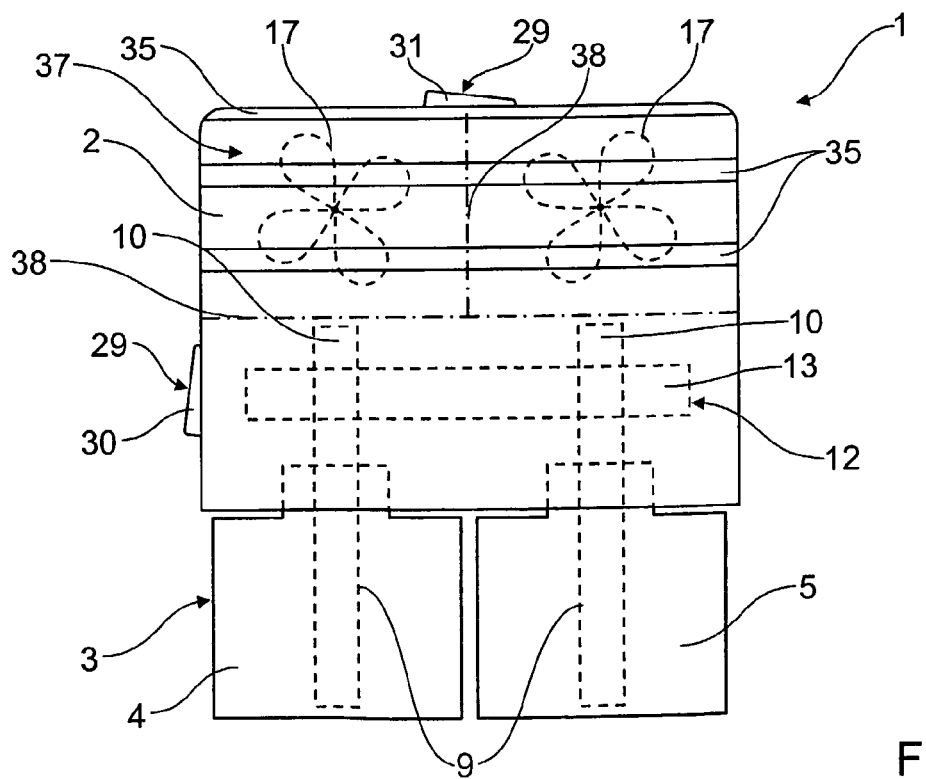
FIG. 6 is a schematic front view according to FIG. 5 with an alternative embodiment 10 of the evaporation device, having two s.

FIGS. 4 to 6 show an alternative embodiment of the evaporation device 1 which differs from the embodiment of FIGS. 1 to 3 by the heater area 41 being enclosed by housing wall 43 so that the wick end 10 is arranged below housing wall 43 in the area of the ventilation slots 44. Evaporated substance 34 can escape via ventilation slots 44 into a mixing chamber 45 in which air stream 33 impinges upon the substance and propels it towards the ventilation slots 35.

Figure 7:
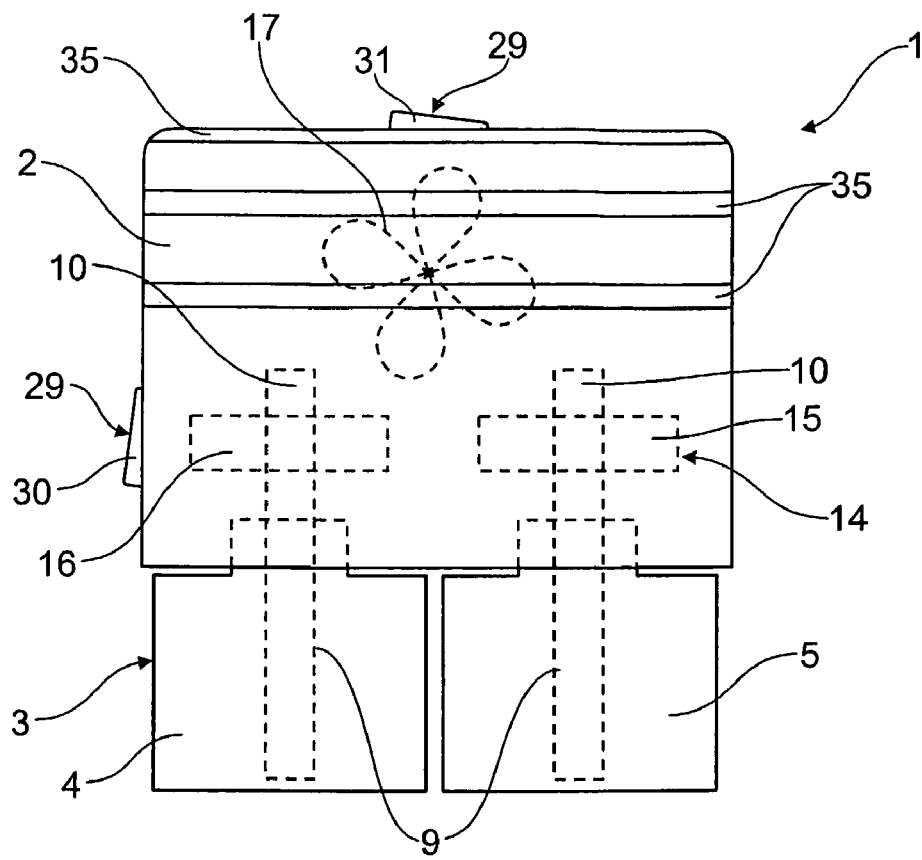
FIG. 7 is a schematic front view of another alternative embodiment of an evaporation device with a separate heater for every wick end.
Figure 9:
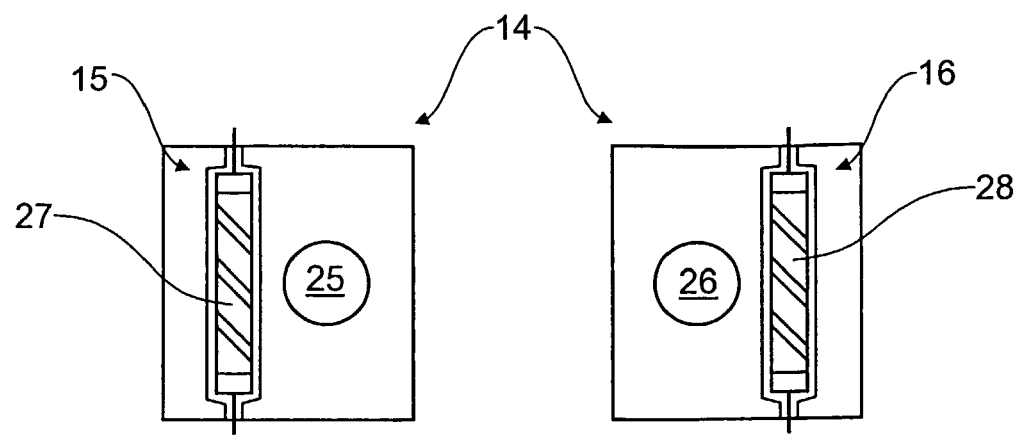
FIG. 9 an alternative embodiment of a heater arrangement in accordance with FIG. 7 with two separate heaters.

FIG. 7 shows another alternative embodiment of the evaporation device 1 which provides for an alternative heater arrangement 14, featuring a first heater 15 and a second heater 16. One heater is assigned to each wick end 10. The structure of heaters 15 and 16 is shown, by way of example, in FIG. 9 which shows that each heater has a wick recess 25, 26. Each wick recess is assigned to an electrical resistance element 27, 28. Resistance elements 23, 24 of FIG. 8, as well as resistance elements of FIG. 9 are preferably film resistors. Of course, other electrical resistance elements can also be used, such as PTC resistance elements.

With evaporation devices 1 described above, an evaporation can be advantageously performed wherein an aromatic is incorporated in one of the two receptacles 4, 5, or in one of the two receiving chambers 7, 8, with an insecticide being incorporated in the other. Via a timer device provided in control unit 11, evaporation can then take place using a programmable microprocessor included in control unit 11, or in connection with a manual switching arrangement as well. In this manner, the aromatic, or the perfume will be evaporated during the day and switched over to an overnight operation for evaporation of the insecticide at a specified time. Such nighttime evaporation of insecticides can be performed for a specifiable time span, and then switched over again to the evaporation of the aromatic. For example, the programming can be performed so that the unevaporated substance will also be evaporated at least at specific times, e.g., periodically. Due to the manual switching, or the controlled switching via the timer device, of the blowers, the required and desired concentration of aromatic or insecticide will be reached in a fast and simple manner after the switch-over in a simple manner.

In accordance with another advantageous process design, two different insecticides can also be placed in receptacles 4, 5 or in receiving chambers 7, 8 which are designed for different types of insects. For example, mosquitoes and flies. Due to the timer-controlled switching of blower 17, or due to the timer-controlled switching as a function of a manual switch actuation, it is now possible to provide, in a considerably shorter period of time after switching over from one to the other substance, a required high concentration of insecticides which require a higher concentration to develop their effect. In this manner the evaporation device can prevent the undesirable continuous release of the insecticide over a long period of time.

Figure 11:
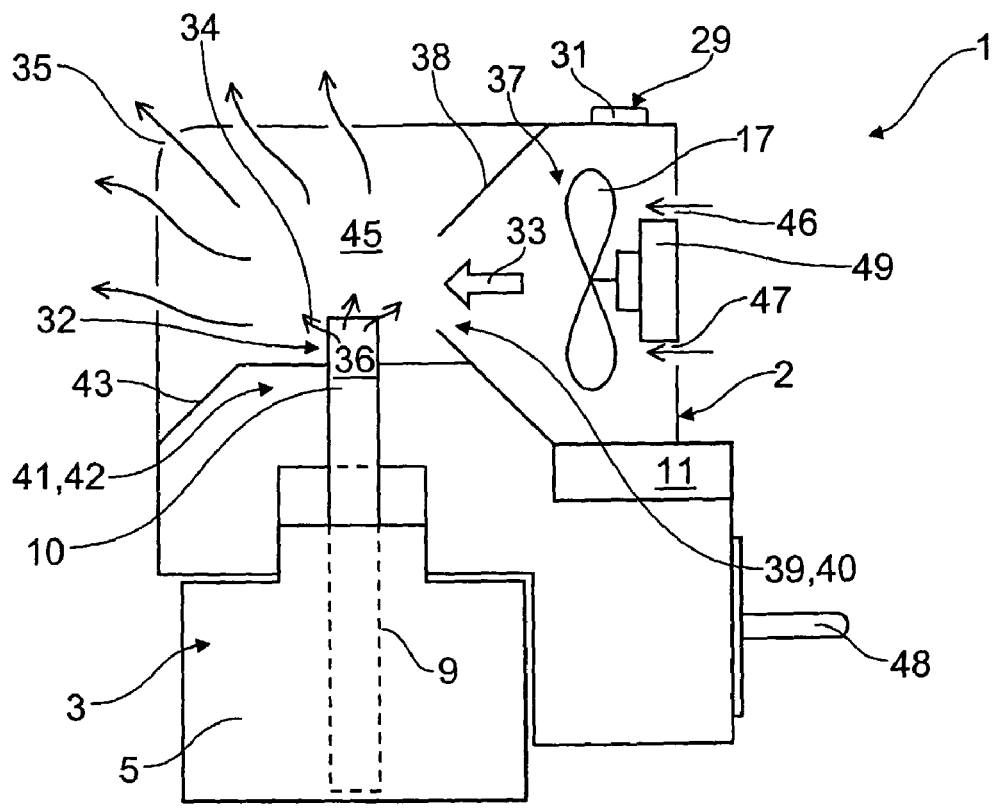
FIG. 11 an alternative embodiment of an evaporation device with a heater arrangement heating the air stream.

FIG. 11 shows another embodiment of an evaporation device 1 in accordance with the invention wherein the heater arrangement features a heating element 49 generally enclosed in a partial housing area 37 so that the air inlet stream taken in by blower 17, shown by arrows 46, 47, will be heated creating a heated air stream 33. The heated air stream leaves the housing area 37 via the nozzle 40, 35. The stream will advantageously impinge upon the wick end(s) in mixing chamber 45 arranged in the flow area to evaporate the corresponding substance away from the wick end. In particular, this arrangement is advantageous in combination with an evaporation device in which a single receptacle is used for one substance to be evaporated. Especially in combination with two receiving chambers for different substances, it is advantageous to assign to each individual wick end 10 a separate blower 17 to ensure that the desired substance will also be evaporated when blower 17 is actuated. Here again it is possible to completely switch off blower 17, manually or timer-controlled, so that the evaporation will be performed without the addition of heat. Because, as shown in FIG. 11, there is no heater arrangement provided in this case in the area of the wick end 10. Alternatively, a heater arrangement can be provided for heating the wick in addition to the heating element 49 heating the air stream. This results in a particularly advantageous effective and fast evaporation of the substance(s) to be evaporated.

While a preferred embodiment of the invention has been described using specific terms, such description is for illustrative purposes only, and it is to be understood that changes and variations may be made without departing from the spirit or scope of the following claims.

What is claimed is:

1. An evaporation device for evaporating volatile substances such as aromatics and/or insecticides comprising:
   a housing;
   a receptacle arrangement carried by the housing having two receiving chambers for substances to be evaporated;
   wicks inserted into the receiving chambers having wick ends protruding from the receiving chambers to provide wick end evaporation areas in which evaporated substance is present;
   a heater arrangement carried in the housing for providing heat to the protruding wick ends adjacent said wick end evaporation areas for evaporation;
   at least one blower for generating an air stream;
   a tapered nozzle positioned generally transverse to said wick end evaporation areas for creating a targeted air stream directed across said evaporation areas to entrain and carry said evaporated substance out of said housing; and
   a control unit for controlling the heater arrangement to evaporate the substances and for controlling the blower to be switched on at defined evaporation times.

2. The device of claim 1 wherein the blower is associated with a wick end evaporation area; and a said nozzle directs said targeted air stream entraining the evaporated substance at the wick end evaporation area and conveys the substance to an air outlet of the housing.

3. The device of claim 2 including a plurality of blowers wherein a separate blower is associated with each wick end evaporation area so that a targeted air stream is supplied to each evaporation area when the associated blower is switched on.

4. The device of claims 1 including an interior housing wall for at least partially enclosing the blower in a partial housing area; and said tapered nozzle includes an air stream passage opening defined in the partial housing area for targeting the air stream toward the wick end evaporation area.

5. The device of claim 4 wherein the interior housing wall includes an inclined wall that forms a part of said tapered nozzle for air stream passage.

6. The device of claims 1 wherein the heater arrangement includes a heating block having an individual heating block area for each wick end.

7. The device of claim 6 wherein the individual heating block areas are thermally isolated from each other by at least one air gap between the individual heating block areas.

8. The device of claim 7 wherein each heating block area has a wick passage through which an associated wick end protrudes.

9. The device of claim 8 wherein each heating block area has assigned at least one electrical heating element controllable by means of the control unit.

10. The device of claims 1 wherein the heater arrangement is formed by individual heaters at a distance from each other and one of the heaters is assigned to each wick end.

11. The device of claim 10 wherein the heater arrangement includes a heater block having wick passages through which the assigned wick ends protrude.

12. The device of claim 10 where the heaters include an electrical resistance heating element controllable by the control unit.

13. The device of claim 1 wherein the control unit includes a timer switch device and a programmable microprocessor coupled with the timer device and integrated into the housing.

14. The device of claim 1 wherein the control unit includes a manual switch arrangement for switching the heater arrangement and the blower, and a timer switch device coupled with the manual switch arrangement so that upon actuation of the heater arrangement the blower can be switched on for a prescribed time.

15. The device of claim 14 wherein the manual switch arrangement includes a manual heater switch switching on the heater arrangement and a manual blower switch for switching on the blower.

16. The device of claim 15 wherein the control unit controls the heater arrangement to provide that no substance is evaporated, that one substance is evaporated, or that several substances are evaporated at the same time.

17. The device of claim 14 wherein the manual switch arrangement has a manual blower switch for controlling the blower in combination with the timer device to be on for a prescribed evaporation time when the heater arrangement is switched on.

18. The device of claim 1 including a housing heating area defined by said interior housing wall; a wick end heating area generally enclosed within the housing heating area; the heating arrangement and wick end being disposed in the wick end heating area and housing heating area; and the housing heating area having at least one ventilation slot for releasing the evaporated substance.

19. The device of claim 18 wherein the ventilation slot of the housing heating area is formed in the housing wall and opens into the targeted air stream passage; and including a mixing chamber in which the targeted air stream impinges upon said evaporated substance and in mixed for delivery of the substance to an air outlet of the housing.

20. The device of claim 1 wherein the receptacle arrangement is formed by one of several separate receptacles which provide the receiving chambers and by a single receptacle having a plurality of receiving chambers.

21. The device of claim 1 including one of a connection plug integrated with the house and a connection plug coupled with via a cable to power the heating arrangement and blower.

22. The device of claim 1 wherein the heater arrangement has at lest one heating element arranged in the housing so that the air stream generated by the blower is heated to create a hot air stream that impinges upon a wick end protruding from a receptacle for a substance to be evaporated.

23. The device of claim 1 including two receiving chambers, an aromatic contained in a first receiving chamber, and an insecticide contained in a second receiving chamber; and that the heater arrangement is controlled by the control unit, having a timer switch device so that the aromatic and the insecticide are periodically and alternately evaporated for a period of time prescribed by the timer device.

24. The device of claim 23 wherein the blower is switched on for a prescribed period of time defined by the timer device at the corresponding switchover time.

25. The device of claim 1 including two receiving chambers, a first insecticide contained in a first receiving chamber, a second insecticide contained in a second receiving chamber, the second insecticide being different from the first insecticide, and the heater arrangement is controlled by the control unit having a timer switch device so that the two insecticides are periodically and alternately evaporated for a period of time prescribed by the timer device.

26. An evaporation device for evaporating volatile substances such as aromatics and/or insecticides comprising:
 a housing;
 a receptacle arrangement carried by the housing having two receiving chambers for substances to be evaporated;
 wicks inserted into the receiving chambers having wick ends protruding from the receiving chambers;
 a heater arrangement carried in the housing for providing heat to the protruding wick ends;
 wick end evaporation areas adjacent wick ends in which an evaporated substance exists;
 at least one blower for generating an air stream;
 a control unit for controlling the heater arrangement to evaporate the substances and for controlling the blower to be switched on at defined evaporation times; and
 at least one tapered interior wall disposed between the blower and the protruding wick ends and forming a nozzle passage positioned generally transverse to said wick end evaporation areas for creating a targeted generally transverse air stream that impinges upon the wick end evaporation areas.

27. The device of claim 26 including a mixing chamber disposed in the housing above the interior housing wall in which said evaporated substance and the air stream mix before exiting the housing.

28. An evaporation device for evaporating volatile substances such as aromatics and/or insecticides comprising:
 a housing;
 a receptacle arrangement carried by the housing having two receiving chambers for substances to be evaporated;
 wicks inserted into the receiving chambers having wick ends protruding from the receiving chambers to provide at least one wick end evaporation area in which an evaporated substance is present;
 a heater arrangement carried in the housing for providing heat to the protruding wick ends;
 at least one blower for generating an air stream;
 a control unit for controlling the heater arrangement to evaporate the substances and for controlling the blower to be switched on at defined evaporation times;
 at least one tapered interior wall disposed between the blower and the evaporation area forming a nozzle passage positioned generally transverse to said wick end evaporation area by which a targeted generally transverse air stream is directed toward and entrains said evaporated substance and
 at least one interior housing wall at least partially separating the targeted air stream and the heating arrangement to avoid cooling of the heating arrangement.

29. The device of claim 28 including a mixing chamber disposed at the exit of the nozzle passage in the housing and above the heating arrangement in which said evaporated substance and the air stream mix before exiting the housing.

* * * * *